United States Patent
Siewerdsen et al.

(10) Patent No.: US 12,039,738 B2
(45) Date of Patent: Jul. 16, 2024

(54) MULTI-MOTION COMPENSATION FOR HIGH-QUALITY CONE-BEAM CT OF THE HEAD

(71) Applicant: THE JOHNS HOPKINS UNIVERSITY, Baltimore, MD (US)

(72) Inventors: Jeffrey H. Siewerdsen, Baltimore, MD (US); Wojciech Zbijewski, Baltimore, MD (US); Alejandro Sisniega, Baltimore, MD (US); Joseph Webster Stayman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 713 days.

(21) Appl. No.: 17/056,639

(22) PCT Filed: May 17, 2019

(86) PCT No.: PCT/US2019/032834
§ 371 (c)(1),
(2) Date: Nov. 18, 2020

(87) PCT Pub. No.: WO2019/222606
PCT Pub. Date: Nov. 21, 2019

(65) Prior Publication Data
US 2021/0196215 A1    Jul. 1, 2021

Related U.S. Application Data

(60) Provisional application No. 62/673,271, filed on May 18, 2018.

(51) Int. Cl.
*G06T 7/20*         (2017.01)
*A61B 6/00*         (2024.01)
(Continued)

(52) U.S. Cl.
CPC .............. *G06T 7/20* (2013.01); *A61B 6/032* (2013.01); *A61B 6/4021* (2013.01);
(Continued)

(58) Field of Classification Search
CPC ............ G06T 7/20; G06T 2207/10081; G06T 2207/20201; G06T 2211/412; G06T 7/32;
(Continued)

(56) References Cited

U.S. PATENT DOCUMENTS 10,098,600 B2 * 10/2018 Ning ................. A61B 6/481
11,564,654 B2 *  1/2023 Gorges .............. A61B 6/583
(Continued)

FOREIGN PATENT DOCUMENTS

CA       3095109 A1 *  9/2019   ............ A61B 6/032
EP       2131212 A2 * 12/2009   ......... A61B 5/04284
WO  WO-2020028352 A1 *  2/2020   ............ A61B 5/055

OTHER PUBLICATIONS

Cardiac C-Arm Computed Tomography: Motion Estimation and Dynamic Reconstruction—2009 (Year: 2009).*
(Continued)

*Primary Examiner* — Nizar N Sivji

(57) ABSTRACT

The present invention is directed to a method of multi-motion compensation for high-quality cone-beam CT of the head. A multi-stage approach is incorporated that includes a pre-conditioning stage in which an initial estimation of the motion trajectory is obtained with 3D-2D registration using the motion-contaminated CBCT and projection data. In the present invention, the motion-contaminated CBCT is used as a basis for 3D-2D registration in the pre-conditioning stage to capture large amplitude, rapid movements of the head and provide better initialization of the autofocus solution.

18 Claims, 5 Drawing Sheets

(51) Int. Cl.
*A61B 6/03* (2006.01)
*A61B 6/40* (2024.01)
*A61B 6/50* (2024.01)

(52) U.S. Cl.
CPC ............ *A61B 6/4085* (2013.01); *A61B 6/501* (2013.01); *A61B 6/5205* (2013.01); *A61B 6/5264* (2013.01); *G06T 2207/10081* (2013.01); *G06T 2207/20201* (2013.01)

(58) Field of Classification Search
CPC ..... G06T 11/005; A61B 6/032; A61B 6/4021; A61B 6/4085; A61B 6/501; A61B 6/5205; A61B 6/5264
See application file for complete search history.

(56) References Cited

U.S. PATENT DOCUMENTS

2017/0238897 A1* 8/2017 Siewerdsen ............ A61B 6/466
2019/0216409 A1* 7/2019 Zhou ...................... A61B 6/032

OTHER PUBLICATIONS

Technical Note: Accelerated nonrigid motion-compensated isotropic 3D coronary MR angiography—2017 (Year: 2017).*
Motion Compensation in Extremity Cone-Beam CT Using a Penalized Image Sharpness Criterion Published on May 7, 2017 (Year: 2017).*
Xu et al., 2016 Modeling and design of a cone-beam CT head scanner using task-based imaging performance optimization. Phys. Med. Biol. 61 3180.
Sisniega et al., 2015 High-fidelity artifact correction for cone-beam CT imaging of the brain. Phys. Med. Biol. 60 1415.
Dang et al., 2015 Statistical reconstruction for cone-beam CT with a post-artifact-correction noise model: application to high-quality head imaging. Phys. Med. Biol. 60 6153.
Jang et al., 2017 Head motion correction based on filtered backprojection for x-ray CT imaging. Med. Phys. 12705.
Jacobson et al., 2008 Compensating for head motion in slowly-rotating cone beam CT systems with optimization transfer based motion estimation. IEEE Nucl. Sci. Symp. Conf. Rec., pp. 5240.
Sisniega et al., 2017 Motion compensation in extremity cone-beam CT using a penalized image sharpness criterion. Phys. Med. Biol. 62 3712.
Sisniega et al., 2016 Image-based motion compensation for high-resolution extremities cone-beam CT. Proc. SPIE Medical Imaging, 9783, 97830K.
Ouadah et al., 2017 Correction of patient motion in cone-beam CT using 3D-2D registration. Phys. Med. Biol. 62 8813.
Hansen et al., 2004 Evaluating the CMA Evolution Strategy on Multimodal Test Functions, Proc. 8th Int. Conf. Parallel Probl. Solving from Nat.—PPSN VIII, vol. 3242/2004, pp. 282-291.
Cao et al., 2016 Multiresolution iterative reconstruction in high-resolution extremity cone-beam CT., Phys. Med. Biol. 61, 7263.
Dang et al., 2016 Multi-resolution statistical image reconstruction for mitigation of truncation effects: application to conebeam CT of the head., Phys. Med. Biol. 62, 539.
Erdogan et al., 1999 Ordered subsets algorithms for transmission tomography., Phys. Med. Biol. 44 2835.

* cited by examiner

MULTI-MOTION COMPENSATION FOR HIGH-QUALITY CONE-BEAM CT OF THE HEAD

CROSS-REFERENCE TO RELATED APPLICATIONS

This application is a 35 U.S.C. § 371 U.S. national entry of International Application PCT/US2019/032834 having an international filing date of May 17, 2019, which claims the benefit of U.S. Provisional Application No. 62/673,271, filed May 18, 2018, the contents of each of the aforementioned applications are herein incorporated by reference in their entirety.

GOVERNMENT SUPPORT

This invention was made with government support under EB-018896 awarded by the National Institutes of Health. The government has certain rights in the invention.

FIELD OF THE INVENTION

The present invention relates generally to medical imaging. More particularly, the present invention relates to multi-motion compensation for high-quality cone-beam CT of the head.

BACKGROUND OF THE INVENTION

Recent developments in dedicated cone-beam CT (CBCT) demonstrate the feasibility for soft-tissue imaging of the brain with compact CBCT systems through careful system design, advanced artifact correction, and model-based iterative image reconstruction. The resulting portable systems for point of care imaging could enable prompt diagnosis and evaluation of intracranial hemorrhage in traumatic brain injury or stroke.

One of the remaining challenges in brain CBCT is the relatively long image acquisition time (typically 15-60 s) that results in susceptibility to artifacts due to involuntary patient motion. Head motion often presents relatively sudden, large amplitude (>10 mm) trajectories and results in streak artifacts, blurring, and double contours that can confound reliable detection of hemorrhage. Motion compensation methods for such motion patterns and amplitudes have been proposed using fiducial markers or external trackers for motion estimation. However, the use of markers or trackers leads to undesirable disruption of the workflow in point-of-care brain imaging.

An image-based autofocus method has shown successful rigid motion estimation and compensation in extremities CBCT. In such approach, a motion trajectory is estimated by iteratively updating a set of candidate motions that are used to generate a population of reconstructed volumes. The optimization process is guided by minimization of a cost function with an image sharpness term computed on the reconstructed volumes and a regularization term that penalizes motion roughness. The method was successfully applied to brain CBCT for moderate motion amplitudes of ~10 mm. However, the movements of the head encountered in critical care imaging often involves even larger amplitude and rapid displacement, which challenges the autofocus optimization and requires improved preconditioning to converge upon an accurate motion estimate.

An additional challenge in clinical application is the presence of elements in the beam that do not follow the same motion trajectory as the head (e.g. the head holder or "cradle," which remains relatively static during acquisition). This results in artifacts arising from application of the motion trajectory derived from moving elements (i.e., the head) to static elements (i.e., the head holder), even after perfect motion estimation. The artifacts are especially conspicuous when applying model-based iterative image reconstruction approaches, such as PWLS that are important for high-quality soft-tissue imaging, requiring modified reconstruction methods to handle a multi-motion FOV.

Accordingly, there is a need in the art for a method of multi-motion compensation for high-quality cone-beam CT of the head.

SUMMARY OF THE INVENTION

The foregoing needs are met, to a great extent, by the present invention which provides a method for multi-motion compensation for object motion in computed tomography (CT), including executing a pre-conditioning of CT data to initialize motion estimates. The method includes performing a three-dimensional motion estimation using an autofocus optimization based on a predetermined objective function. The method also includes estimating motion trajectory within a process of reconstruction of an image generated from the CT data and performing a reconstruction accommodating multiple fields-of-view in motion estimation.

In accordance with an aspect of the present invention, the method includes estimating the object motion using a pre-conditioning stage taking the form of a 3D-2D registration to yield an estimate of the object motion. The input to the 3D-2D registration is an uncompensated 3D image reconstruction. The 3D-2D registration takes the form of the preconditioning stage comprising a forward projection based on an uncompensated CT image and a Covariance Matrix Adaptation Evolution Strategy (CMA-ES) applied to the forward projection to yield a motion estimate. The motion-contaminated CT is used as a basis for 3D-2D registration in the pre-conditioning stage to capture large amplitude, rapid movements of a subject region and provide initialization of the autofocus solution. The method includes generalizing to two or more subregions of the image. The method also includes generalizing to a continuous distribution of subregions to model deformable motion. The reconstruction takes the form of a Penalized Weighted Least Squares (PWLS) reconstruction. The pre-conditioning stage estimates difficult motion patterns (viz., high-amplitude, sudden motion) via 3D-2D registration of the scan data to an uncompensated 3D reconstruction using the same scan data—i.e., does not require a prior scan.

In accordance with another aspect of the present invention, a Multi-Motion compensation method uses an image sharpness criterion for iterative optimization analogous to conventional autofocus, but accommodates multiple regions of the object following distinct motion patterns. The Multi-Motion compensation method is further generalizable to an arbitrarily large number of regions within the image, the motion patterns for which can be interpreted together in approximation to complex deformable motion. A model-based reconstruction algorithm includes a forward projector implementing multiple independent motions of a set of non-overlapping regions in the field of view.

In accordance with yet another aspect of the present invention, a system for computed tomography (CT) includes a CT scanner configured to obtain CT data. The system includes a non-transitory computer readable medium programmed for executing a pre-conditioning of CT data to initialize motion estimates. The method includes performing a three-dimensional motion estimation using an autofocus optimization based on a predetermined objective function. The method includes estimating motion trajectory within a process of reconstruction of an image generated from the CT data and performing a reconstruction accommodating multiple fields-of-view in motion estimation.

In accordance with still another aspect of the present invention, the method includes estimating the object motion using a pre-conditioning stage taking the form of a 3D-2D registration to yield an estimate of the object motion. The 3D-2D registration takes the form of preconditioning stage comprising a forward projection based on an uncompensated CT image and a Covariance Matrix Adaptation Evolution Strategy (CMA-ES) applied to the forward projection to yield a motion estimate. The motion-contaminated CT is used as a basis for 3D-2D registration in the pre-conditioning stage to capture large amplitude, rapid movements of a subject region and provide initialization of the autofocus solution. The reconstruction takes the form of a Penalized Weighted Least Squares (PWLS) reconstruction. The pre-conditioning stage estimates difficult motion patterns (viz., high-amplitude, sudden motion) via 3D-2D registration of the scan data to an uncompensated 3D reconstruction using the same scan data—i.e., does not require a prior scan. A Multi-Motion compensation method uses an image sharpness criterion for iterative optimization analogous to conventional autofocus, but accommodates multiple regions of the object following distinct motion patterns. The Multi-Motion compensation method is further generalizable to an arbitrarily large number of regions within the image, the motion patterns for which can be interpreted together in approximation to complex deformable motion.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
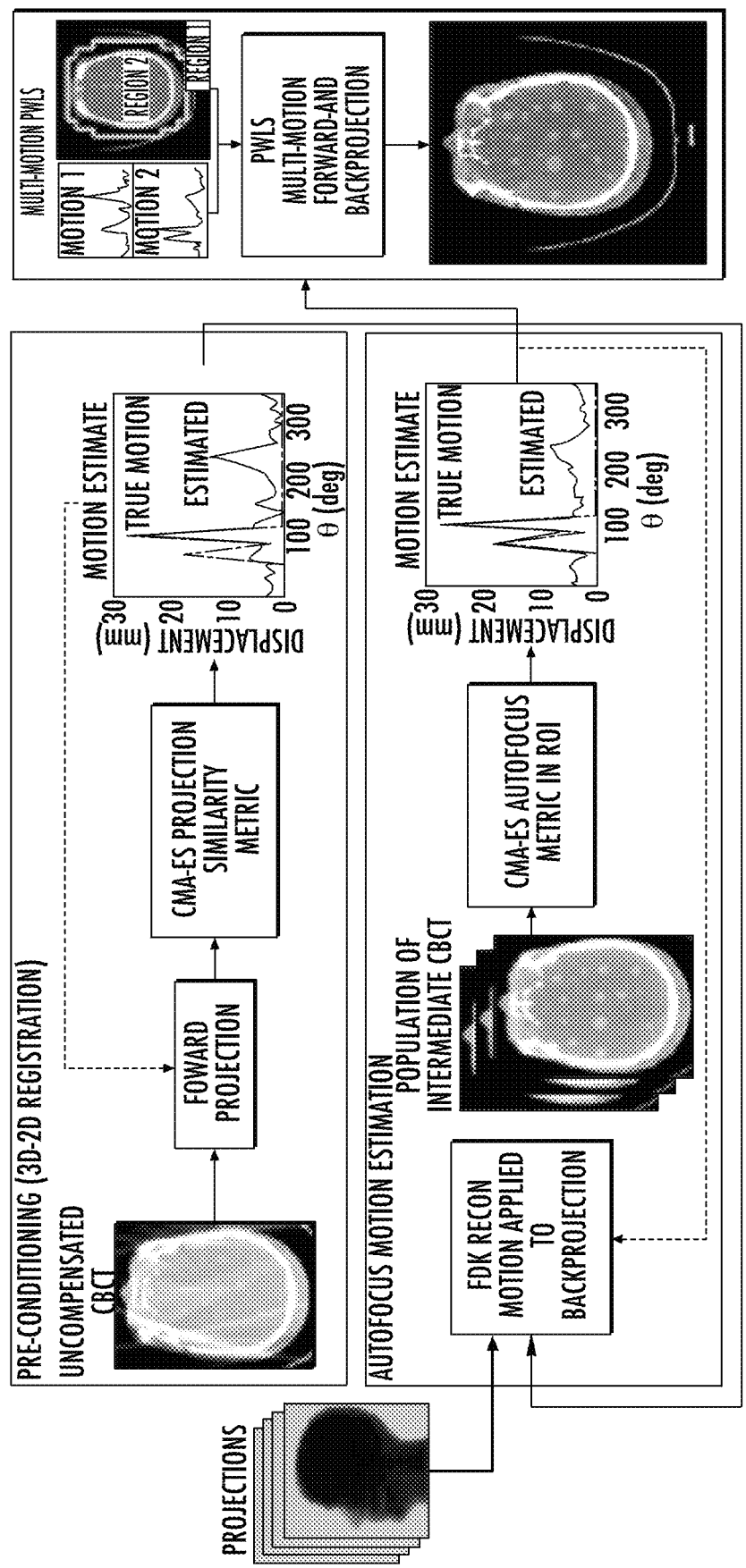
FIG. 1 illustrates a flow diagram of the workflow of the motion estimation and multi-motion reconstruction framework.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method of multi-motion compensation for high-quality cone-beam CT of the head. A multi-stage approach is incorporated that includes a pre-conditioning stage in which an initial estimation of the motion trajectory is obtained with 3D-2D registration using the motion-contaminated CBCT and projection data. In the present invention, the motion-contaminated CBCT is used as a basis for 3D-2D registration in the pre-conditioning stage to capture large amplitude, rapid movements of the head and provide better initialization of the autofocus solution.

The framework includes a modified PWLS reconstruction method accommodating multiple FOVs in motion estimation—in this case, splitting the volume in two regions with a different motion trajectory. The methods are tested in simulation over a broad range of realistic, exactly known motion trajectories and translated to first clinical studies using a prototype CBCT system developed for imaging in the neuro critical care environment. The proposed motion compensation framework for brain CBCT, involves (i) improved pre-conditioning of the motion estimation algorithm, and (ii) an iterative reconstruction approach that includes motion compensation for multiple, independently moving objects in the field of view.

Patient motion during a computed tomography (CT) or cone-beam computed tomography (CBCT) scans leads to significant image artifacts that diminish image quality. To compensate for such artifacts, the present invention is directed to a compensation algorithm that estimates the motion trajectory in the process of image reconstruction. This invention pertains to a new autofocus method (referred to as "Multi-Motion") that accounts for multiple regions/objects undergoing different motion patterns—for example, the patient's head rolling within a head cradle or the distal aspect of the leg (below the knee) moving separately from the proximal aspect of the leg (above the knee). The method generalizes to two or more regions believed to follow distinct motion patterns. The method includes a modified form of forward projection (which is essential to CT or CBCT image reconstruction) suitable for use in model-based reconstruction that divides the 3D volume into multiple regions, each following a different motion pattern.

In the preferred embodiment of the Multi-Motion algorithm described below, a novel pre-conditioning step is included to initialize the motion estimates. The preconditioning is especially useful when the object (and/or regions therein) undergoes motion of high amplitude and/or abrupt change. The novel method for preconditioning uses 3D-2D image registration to yield a coarse estimate (initialization) of object motion. Unlike prior art that requires a motion-free 3D image as input to the 3D-2D registration, our method uses an un-compensated 3D image reconstruction from the same scan. Thus, the 2D projection data are registered to an un-compensated (motion-contaminated) 3D image reconstruction from the same scan data. The resulting 3D-2D registration yields a coarse motion estimate that is sufficient for initialization of the Multi-Motion method and captures high-amplitude, sudden motion components that are otherwise difficult to solve.

The Multi-Motion method is distinct from prior art: unlike conventional autofocus, the Multi-Motion method generalizes to two or more subregions of the image and can further generalize to a continuous distribution of subregions, thereby modeling complex deformable motion; the algorithm does not require any trackers, fiducials, or prior scans to estimate patient motion (i.e. is completely driven by the acquired x-ray CT projection data).

The pre-conditioning stage incorporated within the current preferred embodiment estimates difficult motion patterns (viz., high-amplitude, sudden motion) via 3D-2D registration of the scan data to an uncompensated 3D reconstruction using the same scan data—i.e., does not require a prior scan. The Multi-Motion compensation method uses an image sharpness criterion for iterative optimization analogous to conventional autofocus, but accommodates multiple regions of the object following distinct motion patterns. The Multi-Motion compensation method is further generalizable to an arbitrarily large number of regions within the image, the motion patterns for which can be interpreted together in approximation to complex deformable motion. By comparison, conventional autofocus assumes that the entire object has undergone the same (rigid) motion pattern. The method involves a model-based reconstruction algorithm with a forward projector implementing multiple independent motions of a set of non-overlapping regions in the field of view.

A flowchart for the motion estimation algorithm is shown in FIG. 1. FIG. 1 illustrates a flow diagram of the workflow of the motion estimation and multi-motion reconstruction framework. The pre-conditioning stage estimates large amplitude, sudden motion components via 3D-2D registration. The pre-conditioning stage takes an uncompensated CBCT, and does a forward projection. A CMA-ES projection similarity metric is applied to the projections and forward projection to gain a motion estimate. The second stage uses an autofocus approach to fine-tune the initial motion trajectory by maximizing image sharpness (viz., variance of gradients). FDK recon is used to apply the motion estimate from the pre-conditioning stage to the back projections. A population of intermediate CBCTs are generated. A CMA-ES autofocus metric is then applied to refine the motion estimate. The resulting estimate feeds a multi-motion iterative reconstruction method that solves a separate motion trajectory for different regions of the image—e.g., the outer region (head holder/cradle) and the inner region (head). Subsequently, the modified PWLS method is applied for multi-motion, forward, and backprojection. Motion (T) was considered rigid (6-DoF) for the head, and was modelled as a time-varying motion trajectory using cubic b-spline (B) fitting to a function of projection angle θ:

$$(\theta, j) = \Sigma_{i=0}^{N} c_{ij}(\theta - \theta i) \qquad (1)$$

where j is the degree of freedom (=1, ..., 6), N is the number of spline knots, $\theta_i$ is the projection angle corresponding to each knot, and $c_{ij}$ are the b-spline coefficients to be estimated.

The proposed preconditioning stage aims at approximating large amplitude, rapid components of the motion pattern using 3D-2D registration, by minimizing a cost function:

$$\hat{T}_0 = \text{argmax}_T(l, A(T)\mu) - (T) \qquad (2)$$

where l are the log-corrected projections, A(T) is the forward projection operator for motion trajectory T, GC is the similarity metric for function maximization (in this work gradient correlation, as defined below), and $R_m(T)$ is a regularization term that penalizes abrupt motion, weighted by the scalar $\beta_m$.

Gradient correlation (GC) was defined as:

$$GC(f,m) = \frac{1}{2}\{NCC(\nabla_u f, \nabla_u m) + NCC(\nabla_v f, \nabla_v m)\} \qquad (3)$$

where $\nabla_u$ and $\nabla_v$ are gradient operators in the u and v directions of the projection domain, and:

$$NCC(f, m) \frac{\sum_i (f_i - \bar{f})(m_i - \bar{m})}{\sqrt{\sum_i (f_i - \bar{f})} \sqrt{\sum_i (m_i - \bar{m})^2}} \qquad (4)$$

where f is the fixed image (projection data l), and m is the moving image (forward projection A(T)μ).

The term $R_m(T)$ penalizes the first order difference of the position of the RoI used for motion estimation in subsequent projections:

$$R(T) = \sum_{k=1}^{\theta} \sum_{q=2}^{N_\theta} \sqrt{(x_{k,q}(T) - x_{k,q-1}(T))^2 + (y_{k,q}(T) - y_{k,q-1}(T))^2 + (z_{k,q}(T) - z_{k,q-1}(T))^2} \qquad (5)$$

where $x_{k,q}$, $y_{k,q}$, and $z_{k,q}$ are the coordinates of the k-th corner of the RoI in projection q.

The approximate solution obtained in the initialization stage is used as the initial guess for the autofocus motion compensation. Autofocus motion estimation consists in the maximization of the cost function:

$$\hat{T} = \text{argmax}_T S(T, \mu) - \beta_m R_m(T), \text{ with}$$
$$\text{initialization } \hat{T}^{(0)} = \hat{T}_0 \qquad (6)$$

where S(T, μ) is a metric maximizing image sharpness, in this case the variance of the spatial gradient of the reconstructed volume μ, for motion trajectory T.

The cost functions for both stages (Eqs. 1 and 6) are not convex and exhibit local minima that challenge gradient-based methods. The minimization was performed with the Covariance Matrix Adaptation Evolution Strategy (CMA-ES).

Even in the case of perfect motion estimation, the presence of elements that remain static or follow different motion trajectories than the head introduce artifacts in the reconstructed volume if the reconstruction algorithm assumes that the entire FOV follows the same motion pattern. The present invention includes a "multi-motion" Penalized Weighted Least Squares (PWLS) approach in which the volume is split into a number of regions (in this application, two regions) that follow different motion trajectories.

Conventional PWLS uses the following cost function:

$$\hat{\mu} = \arg_\mu \min \|A\mu - l\|_W^2 + \beta R(\mu) \quad (7)$$

where $\hat{\mu}$ is the image estimate, A is the operator for forward projection, l are the log-corrected projection data, W is the matrix of weighting terms (set to the inverse of the variance of the projection data, which are approximated by the raw projection measurements y, assuming a Poisson distribution), and R is a regularization term that penalizes image roughness and takes the form of a Huber function.

In the present invention, A is decomposed into two forward projection operators (AT1 and AT2), following a derivation similar to the one used for multi-resolution PWLS, as described in [10, 11]. Matrices AT1 and AT2 represent the forward projection operators for regions affected by motion $T_1$ and $T_2$, respectively. The forward model can therefore be written as:

$$\bar{y} = D(g)\exp(-\tilde{A}\mu) = D(g)\exp\left([A_{T_1} A_{T_2}]\begin{bmatrix}\mu_{T_1} \\ \mu_{T_2}\end{bmatrix}\right) \quad (8)$$

where D(g) is a diagonal matrix containing the detector gain, and $\mu_{T1}$ and $\mu_{T2}$ are the subvolumes following motion trajectories $T_1$ and $T_2$, respectively, as illustrated in FIG. 2. As described below, the transition from region 1 to 2 was abrupt (discontinuous)—a reasonable choice since the intermediate region is "air" (a pillow). Ongoing work investigates smooth transition from region 1 to 2. PWLS optimization was performed using the separable quadratic surrogate method with ordered subsets (OS-SQS) with 20 subsets and 50 iterations.

Figure 2A:
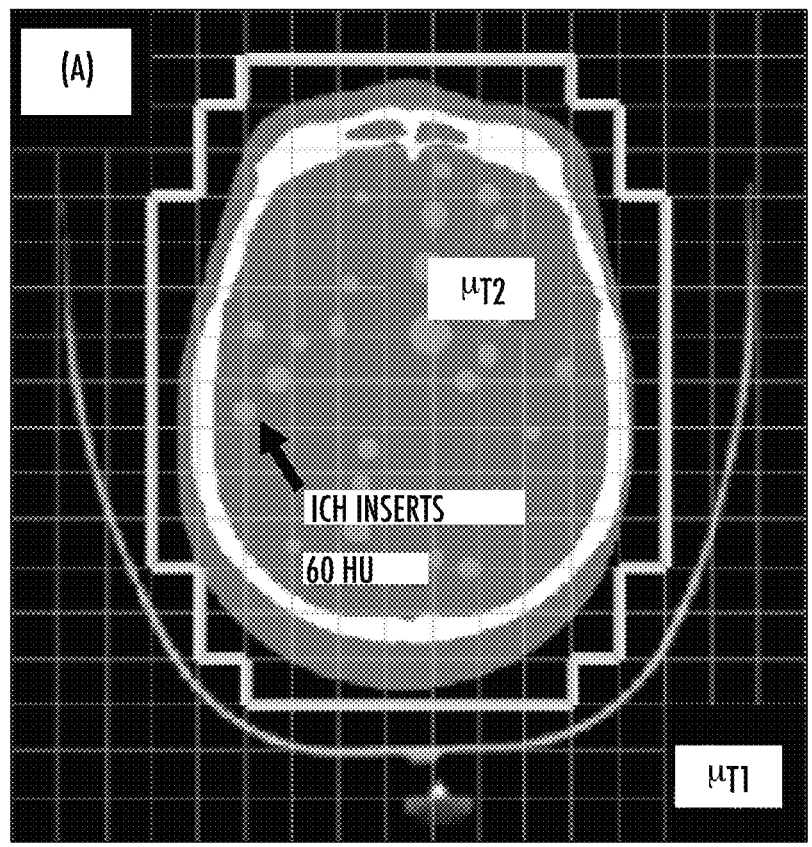
FIG. 2A illustrates a partition view of the image volume into regions with different motion trajectory $\mu_{T1}$ (light grey) and $\mu_{T2}$ (dark grey). The digital head phantom (following T2) presents a natural cranium and spherical intracranial hemorrhages (ICH). The head holder follows a different trajectory (T1) from that of the head, modeling the realistic scenario in which the head rocks or twitches within the cradle.
Figure 2B:
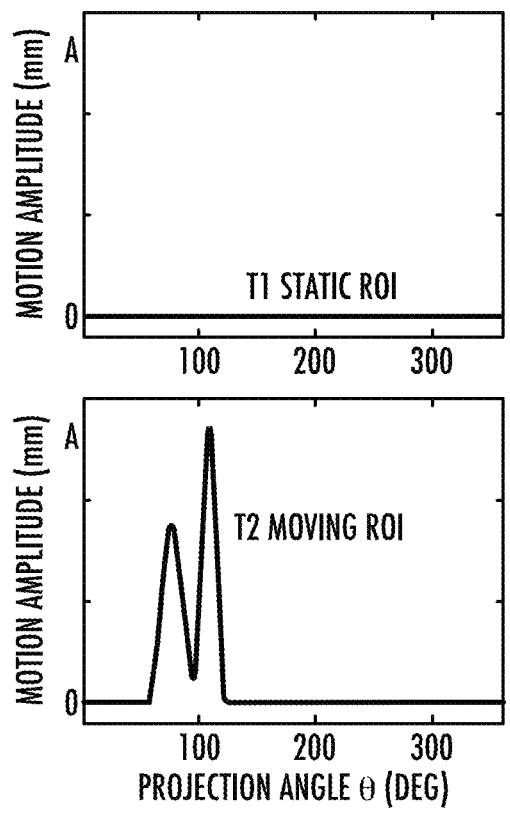
FIG. 2B illustrates graphical views of motion trajectories corresponding to the two subvolumes in FIG. 2A, $\mu_{T1}$ containing the head holder (assumed static) and $\mu_{T2}$, containing the moving head.
Figures 3A, 3B, 3C, 3D, 3E, 3F, 3G, 3H, 3I, 3J:
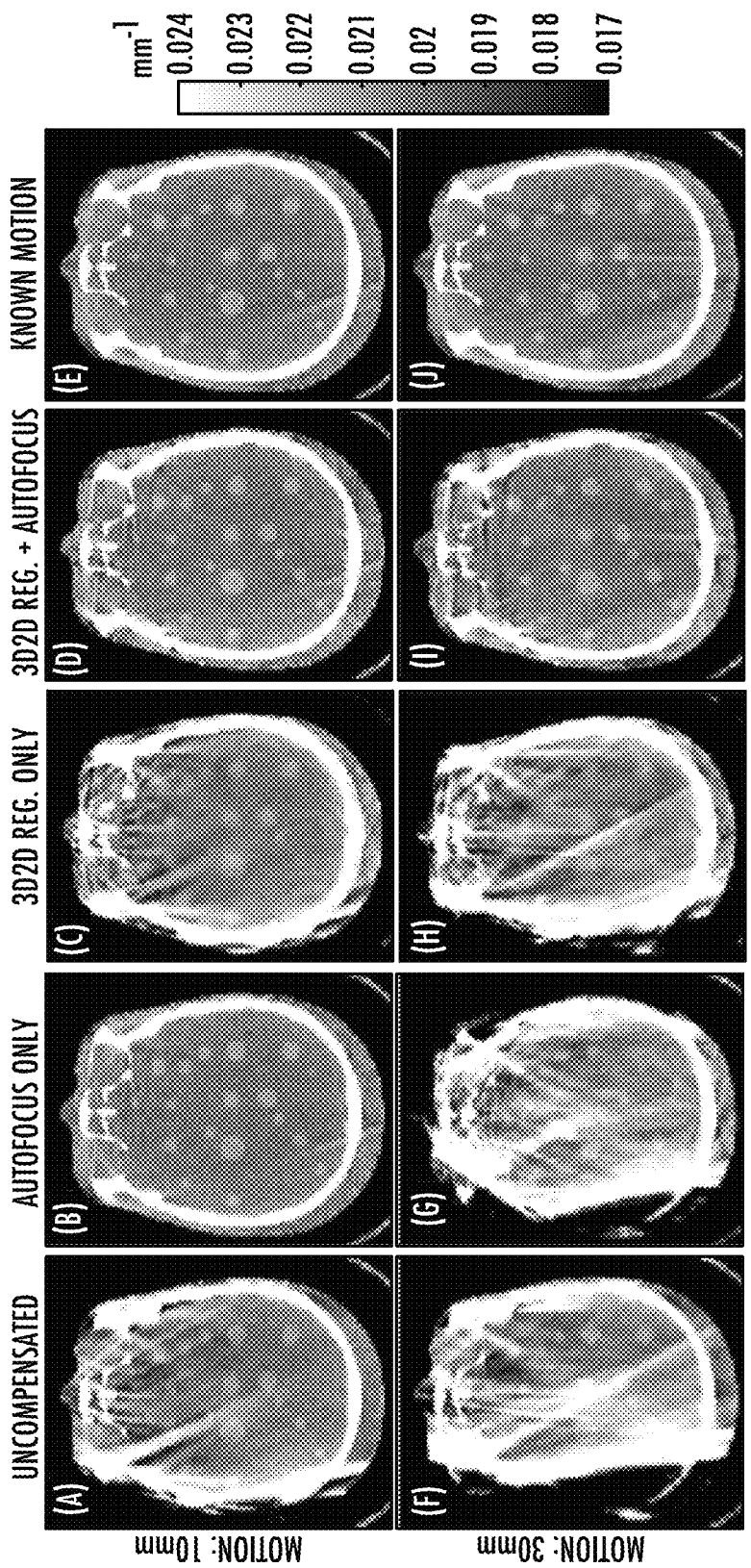
FIGS. 3A-3J illustrate image views of motion compensation in simulated data, for moderate motion amplitude of 10 mm, as illustrated in FIGS. 3A-3E, and large motion amplitude of 30 mm, as illustrated in FIGS. 3F-3J.

FIG. 2A illustrates a partition view of the image volume into regions with different motion trajectory $\mu_{T1}$ (light grey) and $\mu_{T2}$ (dark grey). The digital head phantom (following $T_2$) presents a natural cranium and spherical intracranial hemorrhages (ICH). The head holder follows a different trajectory ($T_1$) from that of the head, modeling the realistic scenario in which the head rocks or twitches within the cradle. FIG. 2B illustrates graphical views of motion trajectories corresponding to the two subvolumes in FIG. 2A, $\mu_{T1}$ containing the head holder (assumed static) and $\mu_{T2}$, containing the moving head.

Performance of motion estimation was evaluated in simulations using a digital head phantom, see FIGS. 2A and 2B, including a heterogeneous brain background with spherical inserts simulating ICH with diameter ranging from 4 to 12 mm, and 60 HU contrast. The brain background is combined with a skull with variable density extracted from an MDCT scan of a real skull.

Motion was simulated with amplitude ranging from A=5 mm to A=30 mm, following the trajectory depicted in FIG. 2B, which itself was derived from a realistic motion pattern measured in clinical data with a prior MDCT of the same patient. Projection data were obtained with and without presence of a (static) head holder, which was modelled from a segmented MDCT scan of an actual head holder used in clinical routine.

Motion estimation was performed using the two-stage approach, with 1000 iterations of the 3D2D registration "pre-conditioning" stage and 10,000 iterations of the "multi-motion" autofocus method, with a population of 10 volumes in CMA-ES optimization, σ=0.5 mm in the first stage, σ=0.05 mm in the second stage, β=0.05, and N=60.

Image reconstructions were performed using the multi-motion PWLS approach in comparison to conventional PWLS for the projection data with and without the head holder. Performance of motion compensation was quantified in terms of structural similarity index (SSIM) computed with single-motion PWLS reconstructions obtained using the estimated and known motion trajectories. Multi-motion PWLS was applied with a moving ROI manually selected on the motion-contaminated reconstruction. Residual artifacts were visually assessed and quantified in terms of RMSD from data reconstructed with the same motion trajectory but not including the head holder.

Figure 4C:
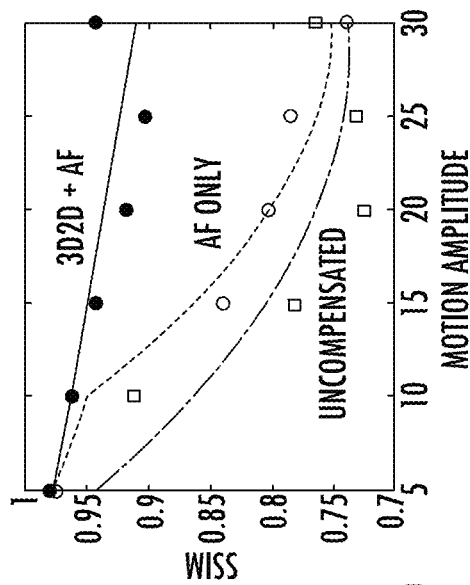
FIG. 4C illustrates a graphical view of SSIM for the resulting motion-compensated images show better performance for the two-stage approach, especially for large amplitude motion.
Figure 4B:
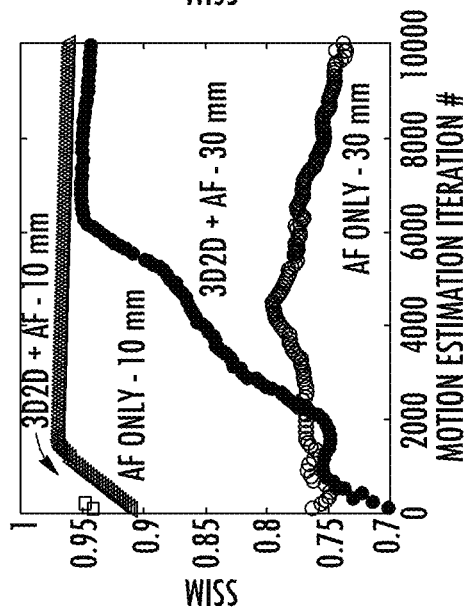
FIG. 4B illustrates a graphical view of SSIM between the current image estimate and that for the known trajectory plotted as a function of iteration number for the autofocus (AF) motion estimation with conventional initialization and with the two-stage approach (3D2D+AF).
Figure 4A:
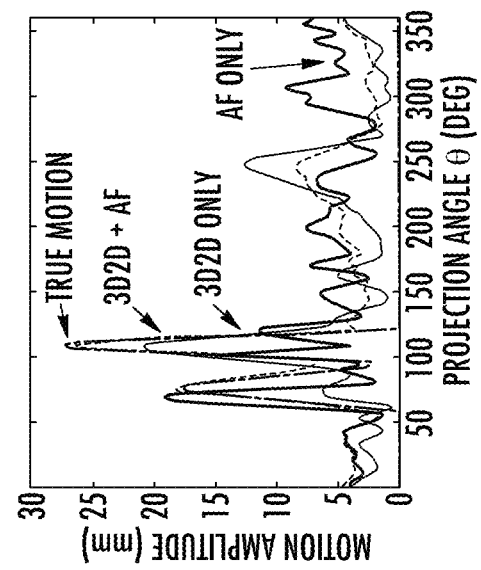
FIG. 4A illustrates motion trajectories obtained with the autofocus motion estimation with no initialization (dark grey curve), with only the 3D2D initialization stage (medium grey) and with the two-stage approach (black), compared to the true motion (light grey).

FIGS. 3A-3J illustrate image views of motion compensation in simulated data, for moderate motion amplitude of 10 mm, as illustrated in FIGS. 3A-3E, and large motion amplitude of 30 mm, as illustrated in FIGS. 3F-3J. FIG. 4A illustrates motion trajectories obtained with the autofocus motion estimation with no initialization (dark grey curve), with only the 3D2D initialization stage (medium grey) and with the two-stage approach (black), compared to the true motion (light grey). FIG. 4B illustrates a graphical view of SSIM between the current image estimate and that for the known trajectory plotted as a function of iteration number for the autofocus (AF) motion estimation with conventional initialization and with the two-stage approach (3D2D+AF). FIG. 4C illustrates a graphical view of SSIM for the resulting motion-compensated images show better performance for the two-stage approach, especially for large amplitude motion.

Results of the proposed motion compensation method are shown in FIGS. 3A-3J and FIGS. 4A-4C. Uncompensated datasets (FIGS. 3A and 3E) show severe motion-induced quality degradation. In the case of moderate motion (10 mm), motion estimation via conventional autofocus (without preconditioning) was sufficient to reduce motion artifacts and achieve image quality comparable to that with exactly known motion (SSIM=0.96). In the case of large motion, however, the approach did not yield an accurate motion estimate (FIG. 3F) and was prone to local minimum, resulting in residual artifacts and SSIM=0.75. The estimation using only the 3D-2D initialization stage of the two-stage approach was insufficient to completely suppress motion artifacts, though it captured the major components of the motion trajectory, as shown in FIG. 4A. This better preconditioning provided a close enough starting point for the autofocus stage, yielding stronger reduction of motion artifact and a motion trajectory closer to the true motion. The image quality achieved with the estimated motion trajectory was comparable to that obtained with the known motion trajectory, resulting in SSIM=0.94. Convergence for the autofocus motion estimation stage is illustrated in FIG. 4B. The pre-conditioned autofocus method showed faster convergence (~500 iterations vs ~1500 iterations for conventional autofocus) for moderate motion amplitude. For large motion amplitude, conventional autofocus showed fairly constant SSIM, indicating failed convergence. Final SSIM for the motion compensated images, as illustrated in FIG.

4C, shows better image quality for the pre-conditioned approach for amplitude larger than 10 mm (minimum SSIM of 0.91).

Figures 5A, 5B, 5C, 5D, 5E, 5F, 5G:
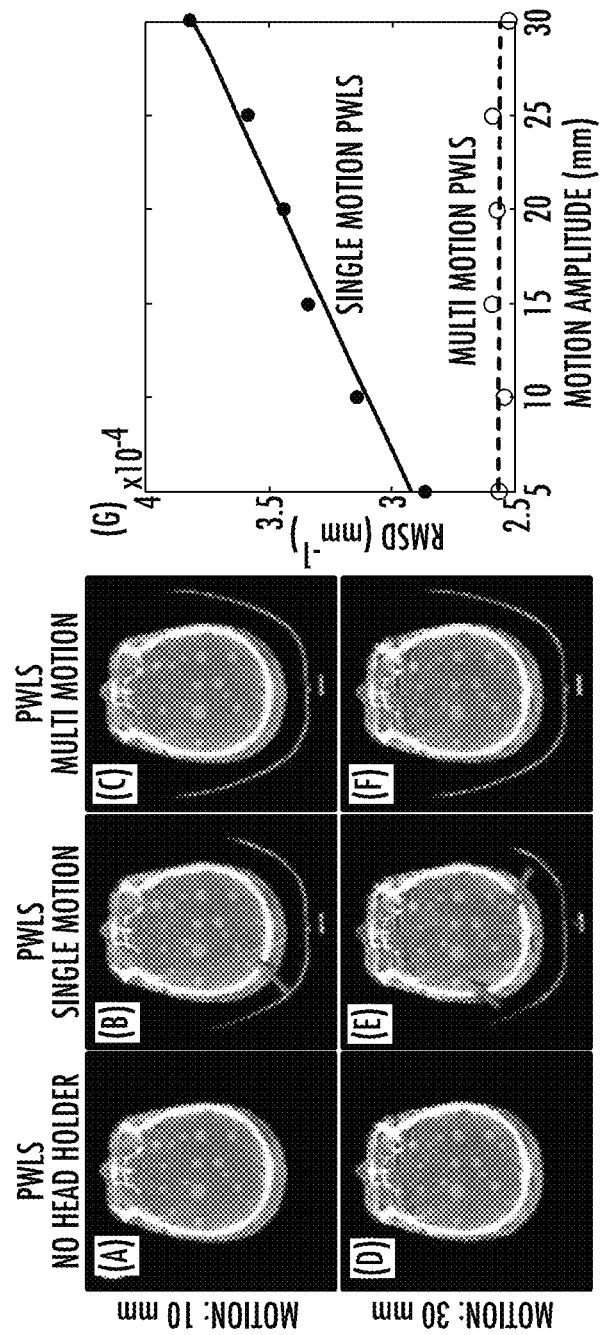
FIGS. 5A-5F illustrate image views of a comparison between single-motion and multi-motion PWLS reconstruction for moderate motion (10 mm amplitude in FIGS. 5A, 5B, and 5C) and large motion amplitude (30 mm in FIGS. 5D, 5E, and 5F).

FIGS. 5A-5F illustrate image views of a comparison between single-motion and multi-motion PWLS reconstruction for moderate motion (10 mm amplitude in FIGS. 5A, 5B, and 5C) and large motion amplitude (30 mm in FIGS. 5D, 5E, and 5F). FIG. 5G illustrates an RMSD (relative to the image not including the head holder) for single- and multi-motion PWLS reconstructions.

Residual artifacts were evident even when using the known motion trajectory, introduced by the assumption that the static head holder follows the same motion as the head. The performance of the proposed multi-motion PWLS method in reducing those artifacts is shown in FIGS. 5A-5G. Even for moderate motion amplitude (10 mm), conventional PWLS resulted in distortion of the head holder shape and streak artifacts at the back of the head (FIG. 5B), yielding RMSD=2.8×10−4 mm−1. Those artifacts are largely mitigated when using the multi-motion reconstruction (FIG. 5C), with image quality comparable to the reconstruction with no head holder (FIG. 5A), and RMSD=2.62×10−4 mm−1. Effects are more noticeable in the case of large motion (30 mm), with successful suppression of the artifacts when using the proposed approach. Using the conventional approach, RMSD (FIG. 5G) increased with motion amplitude, resulting in RMSD=3.81×10−4 mm−1. However, the multi-motion PWLS method yielded RMSD that was invariant with motion amplitude (RMSD=2.56×10−4 mm−1 and RMSD=2.52×10−4 mm−1 for 10 and 30 mm motion, respectively).

The combination of preconditioning (based on 3D-2D registration) and a multi-motion autofocus methods demonstrates the capability to perform purely image-based motion estimation (i.e., without external trackers) in the challenging scenario of high-quality CBCT of the head. Ongoing application to clinical data of a prototype head CBCT scanner shows promising results for motion compensation in clinical environments.

The present invention carried out using a computer, non-transitory computer readable medium, or alternately a computing device or non-transitory computer readable medium incorporated into the scanner. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. Scanners generally have a console which is a proprietary master control center of the scanner designed specifically to carry out the operations of the scanner and receive the imaging data created by the scanner. Typically, this console is made up of a specialized computer, custom keyboard, and multiple monitors. There can be two different types of control consoles, one used by the scanner operator and the other used by the physician. The operator's console controls such variables as the thickness of the image, the amount of tube current/voltage, mechanical movement of the patient table and other radiographic technique factors. The physician's viewing console allows viewing of the images without interfering with the normal scanner operation. This console is capable of rudimentary image analysis. The operating console computer is a non-generic computer specifically designed by the scanner manufacturer for bilateral (input output) communication with the scanner. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for multi-motion compensation for object motion in computed tomography (CT), comprising:
executing a pre-conditioning of CT data to initialize motion estimates, wherein the preconditioning stage includes an initial estimation of a motion trajectory that is obtained using a 3D to 2D registration, and wherein the 3D to 2D registration is made with motion contaminated cone-beam computed tomography (CBCT) and projection data, and wherein the pre-conditioning stage estimates difficult motion patterns using 3D-2D registration of the CT data to an uncompensated 3D reconstruction and does not require a prior scan;
performing a three-dimensional motion estimation using an autofocus optimization based on a predetermined objective function;
estimating motion trajectory within a process of reconstruction of an image generated from the CT data; and
performing the reconstruction of the image generated from the CT data accommodating multiple fields-of-view in motion estimation.

2. The method of claim 1 wherein the input to the 3D-2D registration is an uncompensated 3D image reconstruction.

3. The method of claim 1 wherein the 3D-2D registration takes the form of the preconditioning stage comprising a forward projection based on an uncompensated CT image and a Covariance Matrix Adaptation Evolution Strategy (CMA-ES) applied to the forward projection to yield a motion estimate.

4. The method of claim 3 wherein the motion-contaminated CT is used as a basis for the 3D-2D registration in the pre-conditioning stage to capture large amplitude, rapid movements of a subject region and provide initialization of an autofocus solution.

5. The method of claim 1 further comprising generalizing to two or more subregions of the image.

6. The method of claim 1 further comprising generalizing to a continuous distribution of subregions to model deformable motion.

7. The method of claim 1 wherein the reconstruction takes a form of a Penalized Weighted Least Squares (PWLS) reconstruction.

8. The method of claim 1 wherein the pre-conditioning stage estimates difficult motion patterns using high amplitude or sudden motion.

9. The method of claim 1 wherein a Multi-Motion compensation method uses an image sharpness criterion for iterative optimization analogous to conventional autofocus, and accommodates multiple regions of the object following distinct motion patterns.

10. The method of claim 9 wherein the Multi-Motion compensation method is further applicable to an arbitrarily large number of regions within the image, the motion patterns for which can be interpreted together in approximation to complex deformable motion.

11. The method of claim 1 further comprising a model-based reconstruction algorithm with a forward projector implementing multiple independent motions of a set of non-overlapping regions in the field of view.

12. A system for computed tomography (CT) comprising:
a CT scanner configured to obtain CT data;
a non-transitory computer readable medium programmed for,
executing a pre-conditioning of CT data to initialize motion estimates, wherein the preconditioning stage includes an initial estimation of a motion trajectory that is obtained using a 3D to 2D registration, and wherein the 3D to 2D registration is made with motion contaminated cone-beam computed tomography (CBCT) and projection data, and wherein the pre-conditioning stage estimates difficult motion patterns using 3D-2D registration of the CT data to an uncompensated 3D reconstruction and does not require a prior scan;
performing a three-dimensional motion estimation using an autofocus optimization based on a predetermined objective function;
estimating motion trajectory within a process of reconstruction of an image generated from the CT data; and
performing the reconstruction of the image generated from the CT data accommodating multiple fields-of-view in motion estimation.

13. The system of claim 12 wherein the 3D-2D registration takes a form of a preconditioning stage comprising a forward projection based on an uncompensated CT image and a Covariance Matrix Adaptation Evolution Strategy (CMA-ES) applied to the forward projection to yield a motion estimate.

14. The system of claim 12 wherein a motion-contaminated CT is used as a basis for the 3D-2D registration in the pre-conditioning stage to capture large amplitude, rapid movements of a subject region and provide initialization of the autofocus solution.

15. The system of claim 12 wherein the reconstruction takes a form of a Penalized Weighted Least Squares (PWLS) reconstruction.

16. The system of claim 12 wherein the pre-conditioning stage estimates difficult motion patterns using high amplitude or sudden motion.

17. The system of claim 12 wherein a Multi-Motion compensation method uses an image sharpness criterion for iterative optimization analogous to conventional autofocus, and accommodates multiple regions of the object following distinct motion patterns.

18. The system of claim 17 wherein the Multi-Motion compensation method is further applicable to an arbitrarily large number of regions within the image, the motion patterns for which can be interpreted together in approximation to complex deformable motion.

* * * * *